United States Patent [19]

Ito et al.

[11] Patent Number: 6,124,410
[45] Date of Patent: *Sep. 26, 2000

[54] METHOD FOR PURIFICATION OF ALPHA-OLEFINS FOR POLYMERIZATION USE AND METHOD FOR PRODUCTION OF POLY-ALPHA-OLEFINS

[75] Inventors: Yoshinao Ito; Kazuo Yasuda; Shougo Shimonishi, all of Kuga-gun, Japan

[73] Assignee: Mitsui Chemicals, Inc., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/877,516

[22] Filed: Jun. 17, 1997

Related U.S. Application Data

[63] Continuation of application No. 08/442,964, May 17, 1995, abandoned.

[30] Foreign Application Priority Data

May 19, 1994 [JP] Japan ..................................... 6-105272

[51] Int. Cl.[7] .......................... C07C 7/148; C07C 11/04; C07C 11/06
[52] U.S. Cl. .......................... 526/77; 526/127; 526/160; 585/820
[58] Field of Search ........................... 526/77, 127, 160; 585/820

[56] References Cited

U.S. PATENT DOCUMENTS

| | | |
|---|---|---|
| 2,413,254 | 12/1946 | Soday ..................................... 585/809 |
| 2,497,296 | 2/1950 | Chance ..................................... 585/854 |
| 2,887,472 | 5/1959 | Fotis ..................................... 502/243 |
| 3,160,580 | 12/1964 | Ochenbach et al. ..................... 585/853 |
| 3,175,021 | 3/1965 | Vanselow et al. ....................... 502/344 |
| 3,594,982 | 7/1971 | Pearson . |
| 4,105,588 | 8/1978 | Balducci et al. . |
| 4,614,729 | 9/1986 | Crawford et al. ........................ 526/77 |
| 4,659,792 | 4/1987 | Kashiwa et al. ..................... 526/125.3 |
| 4,835,338 | 5/1989 | Liu . |
| 5,350,817 | 9/1994 | Winter et al. ........................... 526/127 |

FOREIGN PATENT DOCUMENTS

| | | |
|---|---|---|
| 0111911 | 6/1984 | European Pat. Off. . |
| 0379394 | 7/1990 | European Pat. Off. . |

OTHER PUBLICATIONS

Sittig, Polyolefin Resin Processes Gulf Publ. Co., Houston, Texas (1961) pp. 28–31.

*Primary Examiner*—Fred Teskin
*Attorney, Agent, or Firm*—Birch, Stewart, Kolasch & Birch, LLP

[57] ABSTRACT

The invention provides a method for purification of an α-olefin selected from ethylene and propylene for polymerization use which comprises contacting the α-olefin with an alkali metal carried on a support material. The invention further provides a method for production of a poly-α-olefin which comprises polymerizing the thus purified α-olefin in the presence of a polymerization catalyst comprising a transition metal catalyst component and an organometallic catalyst component.

5 Claims, No Drawings

METHOD FOR PURIFICATION OF ALPHA-OLEFINS FOR POLYMERIZATION USE AND METHOD FOR PRODUCTION OF POLY-ALPHA-OLEFINS

This application is a continuation of application Ser. No. 08/442,964 filed on May 17, 1995, now abandoned.

BACKGROUND OF THE INVENTION

1. Field of the Invention

The invention relates to a method for purification of α-olefins, in particular, ethylene or propylene, for polymerization use and a method for production of poly-α-olefins by use of such purified α-olefins.

2. Description of the Prior Art

α-Olefins, in particular, ethylene or propylene, are very useful for the production of widely used polymers, polyethylene or polypropylene. With regard to such an α-olefin for polymerization use, it is necessary that impurities contained therein are removed to purify the α-olefin before it is polymerized.

As one of such methods for purification of α-olefins, there is known a method in which, for instance, propylene which contains carbonyl sulfide as an impurity is contacted with an absorbent composed of nickel carried on a support material thereby to reduce the content of the carbonyl sulfide in the propylene, as is disclosed in Japanese Patent Application Laid-open No. 61-76425.

A further method is also known in which liquid propylene is contacted with metallic nickel at a temperature of 0–80° C. thereby to remove carbonyl sulfide from the propylene together with carbon monoxide, as is disclosed in Japanese Patent Application Laid-open No. 5-70373.

On the other hand, there is also known a method in which a light oil fraction from thermal cracking of heavy oil is first treated with alumina, silica-alumina or, silica to remove impurities such as nitrogen or oxygen compounds, as is disclosed in Japanese Patent Application Laid-open No. 1-259089.

SUMMARY OF THE INVENTION

It is an object of the invention to provide a novel method for purification of an α-olefin, in particular, ethylene or propylene, for polymerization use.

It is a more specific object of the invention to provide an industrially advantageous method for purification of an α-olefin for polymerization use, in particular, ethylene or propylene, which is obtained by thermal cracking of naphtha or fluid catalytic cracking of heavy oil.

It is a further object of the invention to provide a method for production of a poly-α-olefin, in particular, polyethylene or polypropylene, by polymerization of a so purified α-olefin in a high polymer yield.

The other objects and features of the invention will become clear from the following description.

The invention provides a method for purification of an α-olefin selected from ethylene and propylene for polymerization use which comprises contacting the α-olefin with an alkali metal carried on a support material.

DETAILED DESCRIPTION OF THE INVENTION

The support material is exemplified by, for example, oxides of alkaline earth metals such as magnesium oxide (MgO), calcium oxide (CaO), strontium oxide (SrO) or barium oxide (BaO); oxides of rare earth metals such as lanthanum oxide ($La_2O_3$), cerium oxide ($CeO_2$) or yttrium oxide ($Y_2O_3$); metal oxides such as alumina, silica, silica-alumina, thorium oxide (thoria), zirconium oxide (zirconia), zinc oxide (zinc white), titanium dioxide (titania), talc, hydrotalcites or their analogues, diatomaceous earth, sellaites, bentonites or zeolites; metal salts such as potassium carbonate, sodium carbonate, calcium carbonate, magnesium carbonate or potassium borate; or carbonaceous materials such as silicon carbide, graphite or activated carbon.

Among these support materials, magnesium oxide, calcium oxide, alumina, silica, talc, potassium carbonate, sodium carbonate, calcium carbonate, hydrotalcites or their analogues, or activated carbon, are preferred, with potassium carbonate, magnesium oxide, α-alumina, hydrotalcites or their analogues, or activated carbon being most preferred.

For instance, one of the preferred support materials is exemplified by a molded support material prepared by compression molding of a mixture of anhydrous potassium carbonate and carbon. It is preferred that such a molded support material has a pore volume of 22–38%, more preferably 26–33%, and a compression strength of 1–100 kg/cm$^2$G, more preferably 2–80 kg/cm$^2$G. The molded support material may be in the form of granulates, cylinders, tablets, pellets or spheres etc. The molded support material has a particle diameter preferably of not less than 0.5 mm, and more preferably in the range of 1–10 mm.

The alkali metal used is lithium, sodium, potassium, rubidium or cesium, among which is preferred sodium or potassium, with the former being most preferred. The alkali metal is carried on the support material in an amount of 0.1–20% by weight, preferably 0.5–10% by weight, of the support material.

The alkali metal may be carried on the support material by any suitable method, however, it is preferred that an alkali metal is melted and stirred in the presence of the support material in the form of granulates or any other form to carry the alkali metal thereon. Alternatively, an alkali metal may be vacuum-evaporated on the support material.

It is further preferred that the alkali metal thus carried on the support material is treated with an oxygen containing gas to stabilize the alkali metal carried on the support material.

The oxygen containing gas is preferably such a dried make-up gas which contains no moisture and is prepared by diluting oxygen with an inert gas such as nitrgen, helium or argon. The make-up gas has an oxygen content usually of 3–30% by volume. The dried air is usually used as the make-up gas. The dried air may be diluted with nitrogen. The make-up gas having an oxygen content of 5–10% by volume is most preferred since the stabilization operation is carried out easily.

The stabilization of the alkali metal carried on the support material is carried out usually by contacting the alkali metal with the oxygen containing gas at a temperature of 25–200° C., preferably at a temperature of 50–150° C., over a period of about 10–20 minutes, although not limited to. By way of example, the alkali metal carried on the support material is fitted in a vessel and the make-up gas is passed therethrough at a suitable rate. Alternatively, the alkali metal carried on the support material is enclosed in a vessel and the make-up gas is added thereinto. The thus stabilized alkali metal on the support material does not ignite if the alkali metal contacts with water so that it is treated very safely.

The α-olefin is contacted by any method with the alkali metal carried on the support material. However, it is preferred that the alkali metal carried on the support material is fitted in a column and the α-olefin is passed in the form of a gas or liquid through the column. The α-olefin may be only once passed through the column or, may be passed through the column repeatedly or, may be passed through two or more columns. As another method, the alkali metal carried on the support material is placed in a vessel and the α-olefin is added into the vessel followed by agitating the mixture.

The α-olefin is contacted with the alkali metal carried on the support material at a temperature usually of 10–120° C., preferably of 10–80° C. under a normal or decreased or increased pressure usually of not more than 100 kg/cm², with a pressure of 1–50 kg/cm² being preferred.

The method of the invention is especially suitable for the purification of a chemical grade ethylene or propylene which is produced by thermal cracking of naphtha, which may be purified by any known method before it is purified by the method of the invention, or ethylene or propylene produced by fluid catalyst cracking of heavy oils. The method of the invention is in particular suitable for the purification of such propyelene as above mentioned having a propyelene content of not less than 90%.

The α-olefin is purified according to the invention possibly because trace amount of impurities contained in the α-olefin and acting as poisons to a polymerization catalyst is adsorbed to the alkali metal when being contacted therewith and thus is removed therefrom. The polymerization catalyst poison includes, for example, water, carbonyl sulfide (COS), carbon monoxide, nitrogen monoxide, nitrogen dioxide, arsenic hydride ($AsH_3$), antimony hydride ($SbH_3$), ammonia ($NH_3$), halogens or acetylenic compounds, with carbonyl sulfide, arsenic hydride or antimony hydride being very poisoning to the polymerization catalyst.

It is preferred that the α-olefin is dried as much as possible and is then contacted with the alkali metal carried on the support material according to the invention.

The thus purified α-olefin, in particular, ethylene or propylene, is polymerized in the presence of a polymerization catalyst to provide a poly-α-olefin, i.e., polyethylene or polypropylene. In addition to these homopolymers of ethylene or propylene, there may also be produced copolymers of either ethylene or propylene or both of these with at least one of the olefins preferably having 4–20 carbons such as butene-1, hexene-1,4-methylpentene-1, butadiene, norbornene, methylnorbornene, ethylnorbornene, 2,3-dimethylnorbornene, tetracyclododecene, methyltetracyclododecene, ethyltetracyclododecene, 2,3-dimethyltetracyclododecene or styrene. It should be understood that the polyethylene or polypropylene herein the specification includes copolymers of ethylene or propylene which have main repeated units of ethylene or propylene or both.

Any known polymerization catalyst may be used for the polymerization of ethylene or propylene thus purified according to the invention, however, such a high activity catalyst as has an activity of at least 10000 g of polymer/mmol of transition metal is preferred since it provides most desirable results.

Such a high activity catalyst is already known and is preferably composed of a solid transition metal catalyst component comprising a transition metal compound supported on a carrier material and, an organometallic catalyst component.

More specifically, a titanium or zirconium compound is preferred as the transition metal compound, such as titanium tetrahalogenide (e.g., titanium tetrachloride), monoalkoxytitanium trihalogenide (e.g., monobutoxytitanium trichloride), dialkoxytitanium dihalogenide (e.g., dibutoxytitanium dichloride) or tetraalkoxytitanium (e.g., tetrabutoxytitanium), or zirconium homologues. Among these is in particular preferred titanium tetrachloride.

The carrier material used includes, for example, alumina ($Al_2O_3$), silica ($SiO_2$), boron oxide ($B_2O_3$), magnesium oxide (MgO), calcium oxide (CaO), titanium dioxide ($TiO_2$), zinc oxide (ZnO), zinc peroxide ($ZnO_2$), tin oxide ($SnO_2$), barium oxide (BaO), thorium oxide ($ThO_2$), magnesium chloride ($MgCl_2$), magnesium hydroxide ($Mg(OH)_2$), magnesium carbonate ($MgCO_3$), magnesium diethoxide ($Mg(OC_2H_5)_2$), magnesium stearate or, a crosslinked resin such as styrene-divinylbenzene copolymer.

In the preparation of a solid transition metal catalyst component by supporting a transition metal compound on a carrier material, a magnesium compound and an electron donating compound may also be used together with the transition metal compound. The magnesium compound used includes, for example, reductive compounds which have magnesium-carbon bond or magnesium-hydrogen bond or, any other non-reductive compound.

The reductive magnesium compound includes, for example, a dialkylmagnesium such as dimethylmagnesium, diethylmagnesium, dipropylmagnesium or dibutylmagnesium; an alkylmagnesium halide such as ethylmagnesium chloride, propylmagnesium chloride or butylmagnesium chloride; an alkylalkoxymagnesium such as butylethoxymagnesium; and an alkylmagnesium hydride such as butylmagnesium hydride.

In turn, the non-reductive magnesium compound includes, for example, a magnesium halide such as magnesium chloride, magnesium bromide, magnesium iodide; an alkoxymagnesium halide such as methoxymagnesium chloride, ethoxymagnesium chloride, isopropoxymagnesium chloride, butoxymagnesium chloride or octoxymagnesium chloride; an aryloxymagnesium halide such as phenoxymagnesium chloride or methylphenoxymagnesium chloride; an alkoxymagnesium such as ethoxymagnesium, isopropoxymagnesium, butoxymagnesium, n-octoxymagnesium or 2-ethylhexoxymagnesium; an aryloxymagnesium such as phenoxymagnesium or dimethylphenoxymagnesium: and a magnesium carboxylate such as magnesium stearate.

Of the above mentioned magnesium compounds, preferred are non-reductive ones, and more preferred are halogen-containing magnesium compounds. Particularly preferred are magnesium chloride, alkoxymagnesium chloride or aryloxymagnesium chloride.

The magnesium compound as above mentioned, in particular, the non-reductive magnesium compound such as magnesium chloride serves also as a carrier material to support a transition metal compound to form the solid transition metal catalyst component.

Accordingly, it is preferred that the solid transition metal catalyst component is prepared by contacting a transition metal compound (e.g., titanium tetrachloride), a magnesium compound (e.g., magnesium chloride) and an electron donating compound with each other preferably in an inactive organic solvent. The solvent may be the same as used in the polymerizarion of ethylene or propylene purified according to the invention as hereinafter set forth. A preferred solvent is decane, for example.

The electron donating compound includes, for example, nitrogen containing compounds such as organic amines, pyrroles, pyrrolines, pyrrolidines, indoles, pyridines, piperidines, quinolines or isoquinolines; oxygen containing cyclic compounds such as tetrahydrofurans; alcohols of 1–8 carbons (e.g., 2-ethylhexyl alcohol); phenolic compounds of 6–20 carbons; ketones of 3–15 carbons; aldehydes of 2–15 carbons; organic esters of 2–30 carbons (e.g., diisobutyl phthalate or di-2-ethylhexyl phthalate); organic carboxylic acid halides of 2–15 carbons; ethers or diethers of 2–20 carbons; acid amides; nitrites; acid anhydrides (phthalic anhydride); or organic alkoxysilane compounds (e.g., phenyltriethoxysilane).

In turn, the organometallic catalyst component used includes, for example, organometallic compounds of the I to III group metals of the periodic table such as organoaluminum compounds, complexed alkylated compounds of any of the I group metals and aluminum or, dialkylated compounds of any of the II or the III group metals. A number of examples of such compounds used in the preparation of polymerization catalyst are disclosed in Japanese Patent Application Laid-open No. 4-202506.

The organoaluminum compound includes, for example, a trialkylaluminum such as triethylaluminum or tributylaluminum; a dialkylaluminum alkoxide such as diethylaluminum ethoxide or dibutylaluminum buthoxide; an alkylaluminum sesquialkoxide such as ethylaluminum sesquiethoxide or butylaluminum sesquibuthoxide; a dialkylaluminum halide such as diethylaluminum chloride, dibutylaluminum chloride or diethylaluminum bromide; an alkylaluminum sesquihalide such as ethylaluminum sesquichloride, butylaluminum sesquichloride or ethylaluminum sesquibromide; and a dialkylaluminum hydride such as diethylaluminum hydride or dibutylaluminum hydride.

The complexed alkylated compounds of one of the I group metals and aluminum includes, for example, LiAl$(C_2H_5)_4$ or LiAl$(C_7H_{15})_4$.

The dialkylated compound of one of the II or the III group metals may be represented by the formula:

$$R^1R^2M \qquad (I)$$

wherein $R^1$ and $R^2$ are independently a hydrocarbon group having 1 to 15 carbons, preferably 1 to 4 carbons, and M is magnesium, zinc or cadmium.

As a further polymerization catalyst suitably usable in the invention, there may be mentioned, for example, a catalyst comprising a metallocene compound of transition metal and an organooxyaluminum compound, and optionally an organoaluminum compound.

The preferred metallocene compound of transition metal is represented by the following formula:

$$ML_x \qquad (II)$$

wherein M is a metal selected from the IVB group of the periodic table and lanthanoids, and may be exemplified by zirconium, titanium, hafnium, neodymium, samarium or ytterbium, whereas L is a ligand to form coordination compound with the transition metal M at least one of which ligands is a ligand having a cyclopentadienyl group and the other ligands are hydrocarbon group, alkoxy, or aryloxy, each having 1–12 carbons, or halogen atom, trialkylsilyl group, $SO_3R$ (wherein R is a hydrocarbon group of 1–8 carbons which may have inactive substituents thereon such as halogen atom) or hydrogen atom; and x is a valence of the transition metal.

The ligand having a cyclopentadienyl group may be exemplified by, for example, cyclopentadienyl or alkyl substituted cyclopentadienyls such as methylcyclopentadienyl, dimethylcyclopentadienyl, trimethylcyclopentadienyl, tetramethylcyclopentadienyl, pentamethylcyclopentadienyl, ethylcyclopentadienyl, methylethylcyclopentadienyl, propylcyclopentadienyl, methylpropylcyclopentadienyl, butylcyclopentadienyl, methylbutylcyclopentadienyl or hexylcyclopentadienyl. Other examples include indenyl, 4,5,6,7-tetrahydroindenyl or fluorenyl. These groups may carry inactive substituents such as alkyls, halogen atoms or trialkylsilyls thereon.

The metallocene compound usable includes, for example, n-butylcyclopentadienylzirconium dichloride, methylcyclopentadienylzirconium dichloride, 1,3-dimethylcyclopentadienylzirconium dichloride, 1,3-methylbutylcyclopentadienylzirconium dichloride, ethylenebis(indenyl)zirconium dichloride, rac-(i.e., racemic-) dimethylsilylbis(1-(2-methyl-4,5-acenaphthocyclopentadienyl))zirconium dichloride, rac-dimethylsilylbis(1-(2-methyl-4,5-benzoindenyl))zirconium dichloride, rac-dimethylsilylbis(1-(2-methyl-4-isopropyl-7-methylindenyl))-zirconium dichloride, rac-dimethylsilylbis(1-(2-methyl-4,6-diisopropylindenyl))-zirconium dichloride, rac-dimethylsilylbis(1-(2-methyl-4-phenylindenyl))zirconium dichloride or, rac-dimethylsilylbis(1-(2-methylindenyl))zirconium dichloride.

The organooxyaluminum compound used may be a known aluminoxane or an organooxyaluminum compound insoluble in benzene. The known aluminoxane is either linear or cyclic. The linear aluminoxane is represented by the following formula:

(III)

wherein R is an alkyl such as methyl, ethyl, propyl or butyl, preferably methyl or ethyl, with the former being most preferred, and n is an integer of not less than 2, preferably of from 5 to 20, whereas the cyclic aluminoxane is represented by the following formula:

(IV)

wherein R and n are as defined above with respect to the linear aluminoxane.

The aluminoxane may be a mixed alkyl compound comprising a first alkyloxyaluminum unit represented by the formula of (OAl($R^1$)) and a second alkyloxyaluminum unit represented by the formula of (OAl($R^2$)) wherein $R^1$ and $R^2$ are the same as above defined, but different from each other.

The organoaluminum compound used may be the same as those hereinbefore mentioned.

It is most preferred that the polymerization catalyst is prepared by contacting the solid transition metal catalyst component with the organometallic compound, preferably a trialkylaluminum, and the electron donating compound, optionally together with a magnesium compound, in an inactive organic solvent. The electron donating compound may be any one of those mentioned hereinbefore, but an alkylalkoxysilane or arylalkoxysilane or alkylarylalkoxysilane is preferred as the electron donating compound usedat t he stage of preparation of the polymerization catalyst.

The alkylalkoxysilane used includes, for example, trimethylmethoxysilane, trimethylethoxysilane, dimethyldimethoxysilane, dimethyldiethoxysilane, dicyclohexyldimethoxysilane, cyclopentyltrimethoxysilane, dicyclopentyldimethoxysilane, tricyclopentylmethoxysilane, tricyclopentylethoxysilane, dicyclopentylmethylmethoxysilane or dicyclopentylethylmethoxysilane or vinyltrimethoxysilane. The arylalkoxysilane used includes, for example, diphenyldimethoxysilane, diphenyldiethoxysilane, bis(o-tollyl)-dimethoxysilane, bis (p-tollyl)dimethoxysilane, bis(m-tollyl)dimethoxysilane, phenyltrimethoxysilane or phenyltriethoxysilane. The alkylarylalkoxysilane used includes, for example, phenylmethyldimethoxysilane. Other silane compounds such as γ-aminopropyltriethoxysilane, trimethylphenoxysilane or dimethyltetraethoxydisiloxane may akso be used if necessary.

It is most preferred that the polymerization catalyst used is composed of a solid transition metal catalyst component comprising titanium, magnesium, a halogen (especially chlorine) and an electron donating compound together with an organoaluminum catalyst component.

The polymerization of the α-olefin, in particular, ethylene or propylene purified according to the invention provides the corresponding poly-α-olefin in a high yield. Namely, the polymerization of the α-olefin purified according to the invention in the presence of a polymerization catalyst improves the yield of the poly-α-olefin.

The polymerization is carried out usually in the gas or liquid phase. When the polymerization is carried out in a slurry or solution, an inactive hydrocarbon may be used as a reaction solvent. The reaction solvent used includes, for example, aliphatic hydrocarbons such as propane, butane, pentane, hexane, heptane, octane, decane, dodecane or kerosene; alicyclic hydrocarbons such as cyclopentane, cyclohexane or methylcyclopentane; aromatic hydrocarbons such as benzene, toluene or xylene; halogenated hydrocarbons- such as ethylene chloride or chlorobenzene; or a mixture of these. Among these solvents, however, aliphatic hydrocarbons are particularly preferred.

The molecular weight of the resultant polyethylene or polypropylene can be controlled by carrying out the polymerization in the presence of hydrogen, and more specifically, the polymerization in the presence of hydrogen provides polyethylene or polypropylene having a large melt flow rate. The catalyst used retains its high activity by carrying out the polymerization in the presence of hydrogen.

The polymerization is carried out at a temperature usually of from −50° C. to 200° C., preferably from 20° C. to 100° C., under a pressure of from normal pressure to 100 kg/cm$^2$, preferably in the range of about 2 to 50 kg/cm$^2$, either in a batchwise, semicontinuous or continuous manner.

According to the invention, since a high yield of poly-α-olefin is achieved per weight of the solid transition metal catalyst component, the relative amount of residual catalyst, in particular, of the halogen, in the resultant polymer is reduced. Thus, the use of catalyst of the invention permits the omission of operation of catalyst removal and saves time and labor needed therefor. Moreover, the use of such a polymer prevents dies in use from rusting when the polymers are molded.

The invention will be described in more detail with reference to examples, however, the invention is not limited thereto.

EXAMPLE 1
(1) Preparation of Alkali Metal Carried on Support Material
A hydrotalcite analogue Kyoward 1000 (MgO: 34.7%; Al$_2$O$_3$: 19.4%; CO$_2$: 8.7%; H$_2$O: 37.2% by weight; available from Kyowa Kagaku K. K.) was calcined at 500° C. for three hours in the air. The resultant product was found to have a specific surface area of 174 m$^2$/g as measured with a Quantasorb specific surface area measuring instrument (Quantachrome) by a BET single point method. The specific surface area was thus found to be much larger than the value of 121 m$^2$/g the hydrotalcite analogue initially had before it was calcined. The basicity of the calcined product was also measured with an indicator method, and was found to have a strong basicity, as colorless 4-chloroaniline (pKa: 26.5) changed in color to green.

An amount of 25 g of the thus obtained powder was placed in a flask and heated while nitrogen was passed therethrough at a rate of 0.5 liters per hour. Under effective agitation and heating, 3.5 g of metallic sodium was added in limited amounts to the flask over a period of 15 minutes and then the mixture was agitated for another two hours, thereby to provide metallic sodium carried on the hydrotalcite analogue. The amount of carried sodium was found to be 12% by weight of the hydrotalcite analogue.

The basicity of the resultant sodium on the hydrotalcite analogue was measured with an indicator method, and was found to have an extremely strong basicity, as colorless triphenylmethane (pKa: 35.0) changed in color to yellow. The thus sodium carried on the support material was stored in a dried decane.

(2) Purification of Propylene
An amount of 10 g of the sodium carried on the support material was taken out of the dried decane and at once placed in an autoclave, and then an amount of 700 g of chemical grade propylene was added into the autoclave. The mixture was stirred for 24 hours and then the purified gaseous propylene was taken out of the autoclave.

EXAMPLE 2

γ-Alumina (N-615N; having a specific surface area of 215 m$^2$/g and available from Nikki Kagaku K. K.) was used as a support material, and otherwise in the same manner as in Example 1(1), metallic sodium was carried on the γ-alumina in an amount of 9.0% by weight of the γ-alumina.

Propylene was purified by use of the sodium thus carried on the γ-alumina in the same manner as in Example 1(2).

EXAMPLE 3
(1) Preparation of Alkali Metal Carried on Support Material
An amount of 500 g of magnesium nitrate hexahydrates (Mg(NO$_3$)$_2$.6H$_2$O) was dissolved in two liters of water, and a 10% by weight sodium hydroxide solution was added to the resultant solution of magnesium nitrate under stirring until the pH of the mixture reached more than 13. The resultant white colloidal precipitate was washed thoroughly with pure water and dehydrated with filtration.

The resultant cake was dried at 100° C. in a drying instrument for about 20 hours, and was then calcined at 600° C. for three hours with a rotary kiln under a nitrogen stream, thereby to provide a magnesium oxide useful as a support material. The magnesium oxide was stored under a seal of nitrogen.

The basicity of the magnesium oxide was measured with 4-chloroaniline which is known to change in color at a pKa of 26.5. As results, the magnesium oxide caused the change in color of the indicator, and was found to have a basicity of more than pKa of 26.5. The magnesium oxide was further found to have a specific surface area of 51 m$^2$/g by a nitrogen absorption BET method.

An amount of 50 g of powder of the magnesium oxide was placed in a flask and was heated to 250° C. under a nitrogen atmosphere. Under effective agitation, 3.5 g of metallic sodium was added in limited amounts to the magnesium oxide over a period of 15 minutes, followed by agitation for another about two hours, to carry metallic sodium on the magnesium oxide. The amount of carried sodium was found to be 7.0% by weight of the magnesium oxide.

(2) Purification of Propylene

Propylene was purified by use of the sodium thus carried on the magnesium oxide-in the same manner as in Example 1(2).

EXAMPLE 4

(1) Preparation of Alkali Metal Carried on Support Material

The anhydrous potassium carbonate used had a particle size distribution wherein the average particle diameter was 280 μm, the content of particles having a particle diameter of less than 100 μm was 6.9% by weight, the content of particles having a particle diameter of more than 600 μm and less than 1000 μm was 3.4% by weight; a bulk density of 0.68 g/ml; and a pore volume of 0.4 ml/g.

Graphite was added to the anhydrous potassium carbonate in an amount of 1.1% by weight of the potassium carbonate, and was fully admixed therewith. The resultant mixture was molded into a support material in the form of cylindrical tablets having a diameter of 3 mm and a height of 3 mm. The support material had a pore volume of 27% and a compression strength of 6.8 kg/cm$^2$G.

An amount of 97.2 g of the support material was dried at 350° C. in a nitrogen stream. Under a nitrogen atmosphere, 2.8 g of metallic sodium were added to the support material, and the mixture was stirred at 240° C. for five hours, to carry sodium on the support materal.

It was found that a part of metallic sodium reacted with potassium carbonate in the course of carrying the sodium on the support material, and as results, it was found that the carried alkali metals were composed of 48 g-atom % of sodium and 52 g-atom % of potassium and the amount of the alkali metals carried on the support material was 2.7% by weight of the potassium carbonate.

(2) Purification of Propylene

Propylene produced by the fluid catalyst cracking process was purified by use of the alkali metals thus carried on the support material in the same manner as in Example 1(2).

EXAMPLE 5

(1) Preparation of Solid Titanium Catalyst Component A

An amount of 4.76 g (50 mmol) of anhydrous magnesium chloride, 25 ml of decane and 23.4 ml (150 mmol) of 2-ethylhexylalcohol were heated together at 130° C. for two hours to provide a homogeneous solution. An amount of 1.1 g (7.5 mmol) of phthalic anhydride was added to the solution and the mixture was further stirred for one hour to dissolve the phthalic anhydride in the solution.

The solution was cooled to room temperature and was then added drop by drop to 200 ml (1.8 mmol) of titanium tetrachloride kept at −20° C. over a period of one hour. After the addition, the mixture was heated to 110° C. in four hours, and then 2.68 ml (12.5 mmol) of diisobutyl phthalate was added to the mixture at 110° C., followed by agitation for another two hours at the temperature.

After the completion of the reaction, solid material was collected by hot filtration. The solid material was dispersed in 200 ml of titanium tetrachloride again, and the mixture was reacted at 110° C. for two hours again. After the completion of the reaction, solid material was collected by hot filtration again, and then the solid material was fully washed with decane and hexane kept at 110° C. until the filtrate was found to contain no free titanium compound.

The thus prepared solid titanium catalyst component A was stored in the form of a slurry in hexane. A part of the catalyst was dried to determine the composition and was found to be composed of 3.1% by weight of titanium, 56.0% by weight of chlorine, 17.0% by weight of magnesium and 20.9% by weight of diisobutyl phthalate.

(2) Polymerization of Propylene

An amount of 750 ml of purified hexane was placed in a two liter capacity autoclave, and then 2.51 mmol of triethylaluminum, 0.125 mmol of phenyltriethoxysilane and 0.015 mmol (in terms of titanium atoms) of the catalyst component A were charged in the autoclave at room temperature under a propylene atmosphere. After charging 200 ml of hydrogen, the inside temperature was raised to 70° C. and the propylene purified in Example 1(2) was charged into the autoclave, followed by polymerization of the propylene for two hours while the inside pressure was kept at 7 kg/cm$^2$G.

After the polymerization, the resultant polypropylene was separated as white powder by filtration from the resultant slurry and dried to provide 360 g of polypropylene. The catalyst activity was thus found to be 24000 g of polypropylene/mmol of titanium.

COMPARATIVE EXAMPLE 1

Chemical grade propylene before being purified in Example 1(2) was polymerized in the same manner as in Example 5, to provide 180 g of polypropylene in a catalyst activity of 12000 g of polypropylene/mmol of titanium.

EXAMPLE 6

Propylene purified in Example 4 was polymerized in the same manner as in Example 5, to provide 450 g of polypropylene in a catalyst activity of 30000 g of polypropylene/mmol of titanium.

COMPARATIVE EXAMPLE 2

Propylene produced by the fluid catalyst cracking process was polymerized in the same manner as in Example 5, to provide 315 g of polypropylene in a catalyst activity of 21000 g of polypropylene/mmol of titanium.

EXAMPLE 7

An amount of 750 ml of purified n-hexane was placed in a two liter capacity autoclave of stainless steel, and the n-hexane was agitated under a propylene atmosphere for 20 minutes. The inside temperature was raised and when it reached 60° C., 0.2 mmol of triisobutylaluminum, 0.2 mmol (in terms of aluminum atoms) of methylaluminoxane and 0.002 mmol (in terms of zrconium atoms) of rac-dimethylsilylbis(2-methylindenyl)zirconium dichloride were chaged in the autoclave, and the propylene purified in Example 1(2) was charged into the autoclave, followed by polymerization of the propylene for one hour at 70° C. while the inside pressure was kept at 7 kg/cm$^2$G.

After the polymerization, the resultant polypropylene was collocted by filtration from the solvent, washed with methanol and dried at 80° C. for 10 hours, to provide 148 g of polypropylene. The catalyst activity was found to be 74000 g of polypropylene/mmol of zirconium.

COMPARATIVE EXAMPLE 3

Propylene produced by the fluid catalyst cracking process was polymerized in the same manner as in Example 7, to provide 81 g of polypropylene in a catalyst activity of 40500 g of polypropylene/mmol of zirconium.

What is claimed is:

1. A method for producing a poly-α-olefin which comprises:

contacting at a temperature of 10–80° C. and at a pressure of not more than 100 kg/cm² an α-olefin selected from ethylene and propylene with an alkali metal selected from the group consisting of sodium and potassium carried on a support material in an amount of 0.5–10% by weight of the support material, wherein the support material comprises at least one member selected from the group consisting of alumina, silica, magnesium oxide, hydrotalcite and a molded material of a mixture of anhydrous potassium carbonate and carbon, and wherein the alkali metal is disposed on the support material by melting the alkali metal and then carrying the metal on the support material under a nitrogen atmosphere, thereby purifying the α-olefin; and then polymerizing the α-olefin in the presence of a polymerization catalyst comprising a metallocene compound of a transition metal and an organooxyaluminum compound and optionally together with an organoaluminum compound.

2. The method as claimed in claim 1 wherein the catalyst comprises rac-dimethyl-silyl-bis (2-methylindene) zirconium dichloride, an alumninoxane and an organoaluminum compound.

3. The method as claimed in claim 1, wherein the metallocene compound of transition metal is represented by the formula:

$$ML_x$$

wherein M is a metal selected from the IVB group of the periodic table and lanthanoids; L is a ligand to form a coordination compound with the transition metal M, at least one of which ligands is a ligand having a cyclopentadienyl group and the other ligands are hydrocarbon group, alkoxy, or aryloxy, each having 1–12 carbons, or halogen atom, trialkylsilyl group, $SO_3R$ wherein R is a hydrocarbon group of 1–8 carbons with optionally one or more halogen substituents, or R is a hydrogen atom; and x is a valence of the transition metal.

4. The method as claimed in claim 1 wherein the organooxyaluminum compound is an aluminoxane.

5. The method as claimed in claim 1 wherein the organoaluminum compound is a trialkylaluminum.

* * * * *